(12) United States Patent
Cullen et al.

(10) Patent No.: US 8,895,524 B2
(45) Date of Patent: Nov. 25, 2014

(54) VIRAL MICRORNA

(75) Inventors: Bryan R. Cullen, Durham, NC (US); Jennifer Lin Umbach, Durham, NC (US); Donald M. Coen, Cambridge, MA (US); Martha F. Kramer, Cambridge, MA (US); Igor Jurak, Cambridge, MA (US); David Knipe, Auburndale, MA (US)

(73) Assignees: President and Fellows of Harvard College, Cambridge, MA (US); Duke University, Durham, NC (US)

( * ) Notice: Subject to any disclaimer, the term of this patent is extended or adjusted under 35 U.S.C. 154(b) by 594 days.

(21) Appl. No.: 12/736,025

(22) PCT Filed: Mar. 3, 2009

(86) PCT No.: PCT/US2009/035910
§ 371 (c)(1),
(2), (4) Date: Jan. 27, 2011

(87) PCT Pub. No.: WO2009/111493
PCT Pub. Date: Sep. 11, 2009

(65) Prior Publication Data
US 2011/0118332 A1 May 19, 2011

Related U.S. Application Data

(60) Provisional application No. 61/064,387, filed on Mar. 3, 2008.

(51) Int. Cl.
| | | |
|---|---|---|
| *A61K 31/70* | (2006.01) | |
| *C07H 21/02* | (2006.01) | |
| *C07H 21/04* | (2006.01) | |
| *C12N 15/113* | (2010.01) | |
| *A61K 31/7105* | (2006.01) | |
| *C12Q 1/68* | (2006.01) | |
| *C12N 15/11* | (2006.01) | |

(52) U.S. Cl.
CPC ........ *C12N 15/1133* (2013.01); *A61K 31/7105* (2013.01); *C12N 15/111* (2013.01); *C12N 2310/113* (2013.01); *C12N 2310/11* (2013.01); *C12N 2310/111* (2013.01); *C12N 2310/141* (2013.01)
USPC ........ 514/44 A; 536/23.1; 536/24.1; 536/24.5

(58) Field of Classification Search
None
See application file for complete search history.

(56) References Cited

U.S. PATENT DOCUMENTS

| | | | |
|---|---|---|---|
| 7,795,419 B2 * | 9/2010 | Bentwich et al. | 536/24.5 |
| 8,455,633 B2 * | 6/2013 | Bentwich et al. | 536/24.5 |
| 8,481,506 B2 * | 7/2013 | Bentwich et al. | 514/44 A |
| 2001/0009922 A1 | 7/2001 | Faller | |
| 2007/0003575 A1 | 1/2007 | Bentwich et al. | |
| 2007/0054872 A1 | 3/2007 | Reppen et al. | |
| 2007/0154456 A1 | 7/2007 | Bloom et al. | |

OTHER PUBLICATIONS

Notification Concerning Transmittal of International Preliminary Report on Patentability (Chapter 1 of The Patent Cooperation Treaty) issued in connection with International Patent Appln. No. PCT/US2009/035910 filed Mar. 3, 2009.
International Search Report for PCT/US2009/035910, mailed Aug. 12, 2009.

\* cited by examiner

*Primary Examiner* — Sean McGarry
(74) *Attorney, Agent, or Firm* — Nixon & Vanderhye P.C.

(57) ABSTRACT

The present invention relates, in general, to micro RNAs and, in particular, to viral microRNAs expressed by Herpes Simplex Virus 1 (HSV-1) or Herpes Simplex Virus 2 (HSV-2), to agents that inhibit such microRNAs and to methods of treatment based on the use of such agents.

20 Claims, 10 Drawing Sheets

Figure 3A

|  | 293T/LAT (5p/3p) | TG/HSV-1 (5p/3p) |
|---|---|---|
| miR-H2 | 10/265 | 0/94 |
| miR-H3 | 5 | 18 |
| miR-H4 | 61/1266 | 0/0 |
| miR-H5 | 40 | 1 |
| miR-H6 | 0 | 50 |
| miR-H1 | 0 | 0 |

| miRNA | MFOLD hairpin of 150 nucleotides surrounding miRNA |
|---|---|
| hsv2-miR-H2 | ```
UCCCGAC        G       C   -    C        CU UG U
       CCGGCGCGC UCGGUCGCGC UG CCC GGC CAGACU  G  C U
       GGCGCGCG GCCCAGCGCG AC GGG CCG GUCUGG  U  G G
      G                       U  U  Uˆ  A      C- GU G
``` |
| hsv2-miR-H3 | ```
                                      C  ACG
GG-    CCGGCGCGCUCUCGACCGCGG UUCCCGAGU GU  C
       GGCCGCGCGAGGGUUGGGCGC GAGGGUUUA CA  A
CGG                          U         C GGG
``` |
| hsv2-miR-H4 | ```
GGA --     A    A C   C    C   -- U
   GCGC GUCGGGGCGGG GAGUUC CU GGCA GCAUG AC GUG A
   UGCG CGGCCCUGCCC CUCAAG GA CCGU CGUGC UG CGC A
G-- GU     A    C   :   U       C  AC   C
``` |
| hsv2-miR-H5 | ```
CUUCC   U         G C  CAC   UC AAC
     CUCCCGC CCUGCGGGGG CU GGGC  CUGACCU GU    C
     GAGGGCG GGGCGCCCCC GA CCCG  GACUGGA CA    C
A----         C        A  A--       CU CGU
``` |
| hsv2-miR-H6 | ```
G   UC  CUC   GC   A    CG   GCA  A   GAU   C
 GGCG GGGA GCGGAGG CGGAG AUGGAAGG AGGGGAU GG GGAG  C
 CCGC CCUU CGCCUUU GCCUC UACCUUCC UCUUCUA CC CCUC  G
G    CA  U--   UU   C     CG       -.-    -   AGG
``` |

VIRAL MICRORNA

This application is the U.S. national phase of International Application No. PCT/US2009/035910, filed 3 Mar. 2009, which designated the U.S. and claims the benefit to U.S. Provisional Application No. 61/064,387, filed 3 Mar. 2008, the entire contents of each of which are hereby incorporated by reference.

This invention was made with government support under Grant Nos. AI 067968 and PO1 NS03518 awarded by the National Institutes of Health. The government has certain rights in the invention.

TECHNICAL FIELD

The present invention relates, in general, to microRNAs and, in particular, to viral microRNAs, to agents that inhibit the function of such microRNAs and to methods of treatment based on the use of such agents.

BACKGROUND

MicroRNAs (miRNAs) are short regulatory RNAs of ~22 nucleotide (nt) that are expressed by all metazoan eukaryotes. For example, humans encode 420 or more distinct miRNAs. miRNAs are ordinarily first transcribed by RNA polymerase II in the form of a long, capped, polyadenylated transcript called a primary miRNA (pri-miRNA). The miRNA forms part of one arm of an ~80 nt imperfect stem-loop within the pri-miRNA. One pri-miRNA may contain a cluster of several miRNA stem-loops.

The first step in miRNA biogenesis is the recognition of the pri-miRNA hairpin by the nuclear RNase III enzyme Drosha. Drosha cleaves the RNA hairpin approximately two-thirds of the way down the stem, leaving a 2 nt 3' overhang, to liberate an ~60 nt RNA hairpin called a pre-miRNA. This pre-miRNA is exported to the cytoplasm where a second RNase III enzyme, Dicer, binds the base of the pre-miRNA and cleaves ~22 nt away, generating a second 2-nt 3' overhang. The mature miRNA, which forms one strand of the resulting miRNA duplex intermediate, is then incorporated into the RNA induced silencing complex (RISC) where it acts as a guide RNA to target RISC to complementary mRNAs. Once bound to an mRNA, RISC ordinarily can induce mRNA cleavage and degradation, if the complementarity is extensive, or translation arrest, if the complementarity is partial. Post-transcriptional regulation by miRNAs is now known to represent a major level of gene regulation in eukaryotes and miRNAs have been shown to regulate many aspects of cell differentiation and development.

In addition to cells, it is now known that several viruses, including, herpesviruses, encode and express miRNAs in infected cells. Specifically, the human γ-herpesviruses EBV and KSHV have been shown to express 23 and 12 miRNAs, respectively, while the human β-herpesvirus hCMV expresses 11 miRNAs. Less is known about the human α-herpesviruses herpes simplex virus type 1 (HSV-1) and HSV-2.

Initial infection by HSV-1 generally occurs at mucous membranes, frequently around the mouth and lips, and subsequently in trigeminal ganglion neurons that innervate these tissues, and results in a localized infection that resolves, leaving behind trigeminal ganglia that maintain a latent infection with HSV-1. The virus occasionally spontaneously reactivates, often in response to some form of stress, leading to localized painful "cold sores". Once established, latent HSV-1 infection is life-long and, currently, cannot be cured, although the severity of outbreaks can be ameliorated with antiviral drugs. In immunocompromised patients, HSV-1 can become a serious infection, leading to neuronal damage or even death.

In the latently infected trigeminal ganglion, the HSV-1 genome is found exclusively in infected neurons. Within these neurons, HSV-1 is thought to express a ~8.3 kb viral transcript, the so-called minor latency associated (LAT) RNA (Bloom, int. Rev. Immunol. 23:187-198 (2004); Stevens et al, Science 235:1056-1059 (1987)) (FIG. 1). LAT is spliced, to give rise to the abundantly expressed ~2 kb LAT intron, but the remaining exonic—6.3 kb RNA is highly unstable (FIG. 1).

HSV-2 is a close relative of HSV-1, with ~80% sequence identity at the genome level, but generally infects via genital mucous membranes to establish latent infections in the sacral ganglia that innervate the genitals. Like HSV-1, HSV-2 establishes latent infections in neurons and expresses a LAT in those cells.

The present invention results, at least in part, from studies designed to test the hypothesis that HSV-1 and/or HSV-2 LAT might be a pri-miRNA, that is, that one function of LAT may be to generate miRNAs that play a key role in viral latency.

SUMMARY OF THE INVENTION

The present invention relates generally to microRNAs. More specifically, the invention relates to viral microRNAs, including microRNAs expressed by Herpes Simplex Virus 1 (HSV-1) and HSV-2. The invention further relates to agents that inhibit such microRNAs and to methods of treatment based on the use of such agents.

Objects and advantages of the present invention will be clear from the description that follows.

BRIEF DESCRIPTION OF THE DRAWINGS

FIG. 1A. Schematic of the HSV-1 genome expanded to display details of the LAT locus. Relative sizes, locations and orientations of other viral transcripts in this region are indicated. Sequence coordinates of viral miRNAs and restriction enzyme sites are given according to the HSV-1 strain 17 syn genome (NC_001806). All viral miRNAs are in the same orientation as LAT except for miR-H6. An EcoRV-BamHI fragment containing the entire LAT was cloned into pcDNA3, to generate pcDNA3/LAT. TR, terminal repeat; IR, internal repeat; $U_L$, unique long; $U_S$, unique short. FIG. 1B. Northern blot for the ~2.0 kb LAT intron, demonstrating LAT expression after transfection of pcDNA3/LAT into 293T cells. The lower bands show 28S rRNA, a loading control. Small RNAs from this sample were used for cDNA preparation and 454 sequencing.

FIG. 2 discloses SEQ ID NOS 10-14, respectively, in order of appearance.

FIGS. 3A-3C. HSV-1 pre-miRNAs. FIG. 3A. Predicted secondary structures of HSV-1 miRNA precursors, demonstrating the characteristic stem-loops. Mature miRNAs are indicated in red (underlined sequences) and, where observed, passenger strands in blue (dotted sequences). Number of reads of each mature miRNA sequence are indicated. Where the passenger strand was also obtained, these are given as 5p/3p. miR-H1 and miR-H6 were not recovered from transfected 293T cells because pcDNA3/LAT lacks these sequences. FIG. 3A discloses SEQ ID NOS 10-15, respectively, in order of appearance. FIG. 3B. HSV-1 genomic sequence showing the antisense orientation and overlap of mature miR-H6 and miR-H1 (SEQ ID NO: 16). Genomic coordinates are provided in Fig, 1A. FIG. 3C. Quantitative RT-PCR analysis verifying the existence and relative expression of HSV-1 miRNAs in 293T cells transfected with pcDNA3/LAT (blue) (left bar), Vero cells infected with HSV-1 (red) (middle bar), or mouse trigeminal ganglia (TG) latently infected with HSV-1 (yellow) (right bar). miRNA abundances are shown as copies per ng of short-enriched RNAs (<200 nucleotides) The limit of detection for each HSV-1 miRNA is indicated by a dashed line. *; not detected. Horizontal lines indicate background levels for each miRNA assayed.

FIG. 6A. 293T cells were co-transfected with ICP0 and β-arrestin expression plasmids, as well as a synthetic form of the miR-H2 miRNA duplex intermediate. A mutant siRNA, identical to miR-H2 except for three mismatches in the seed region (3M), was used as a negative control. ICP0 and β-arrestin expression were assayed by Western blot. FIG. 6B. Northern analysis of the samples shown in FIG. 6A for ICP0 mRNA expression. 28S rRNA was used as a loading control. FIG. 6C. Sequence homology of miR-H6 (SEQ ID NO: 20) to nucleotides 127, 298 to 127,318 of the predicted ICP4 mRNA (SEQ ID NO: 19). Grey box indicates the miRNA seed region. FIG. 6D. Similar to FIG. 6A, except that 293T cells were co-transfected with an ICP4 expression plasmid and a synthetic miR-H6 duplex intermediate. Here, the miR-H2 duplex intermediate served as a negative control, as ICP4 mRNA has no predicted target sites for miR-H2-3p.

FIG. 7A. Probed with miR-L (5'-GGGCCCCGGGCCGGGCCGCCACG-3' (SEQ ID NO: 1)). FIG. 7B. Same blot as in FIG. 7A, stripped and re-probed for let-7. FIG. 7C. Parallel blot re-probed with miR-H1 after having been probed with the miR-LAT probe, then stripped.

| microRNA | Sequence/Chemistry |
|---|---|
| HSV-1-mir-H2-3p | antimiR<br>5'-AsGsUCGCACUCGUCCCUGGCUCsAsGsGs-chol (SEQ ID NO: 2) |
| HSV-1-mir-H6 | antimiR<br>5'-GsGsGAUGGAAGGACGGGAAsGsUsGs-chol (SEQ ID NO: 3) |

The lower case "s" indicates a phosphorothioate linkage and all nucleotides bear a 2'-OMe modification. The cholesterol (chol) attached to the 3' end of the oligo facilitates cellular uptake. Viral reactivation was efficiently induced in the presence of the antagomirs.

Figure 2:
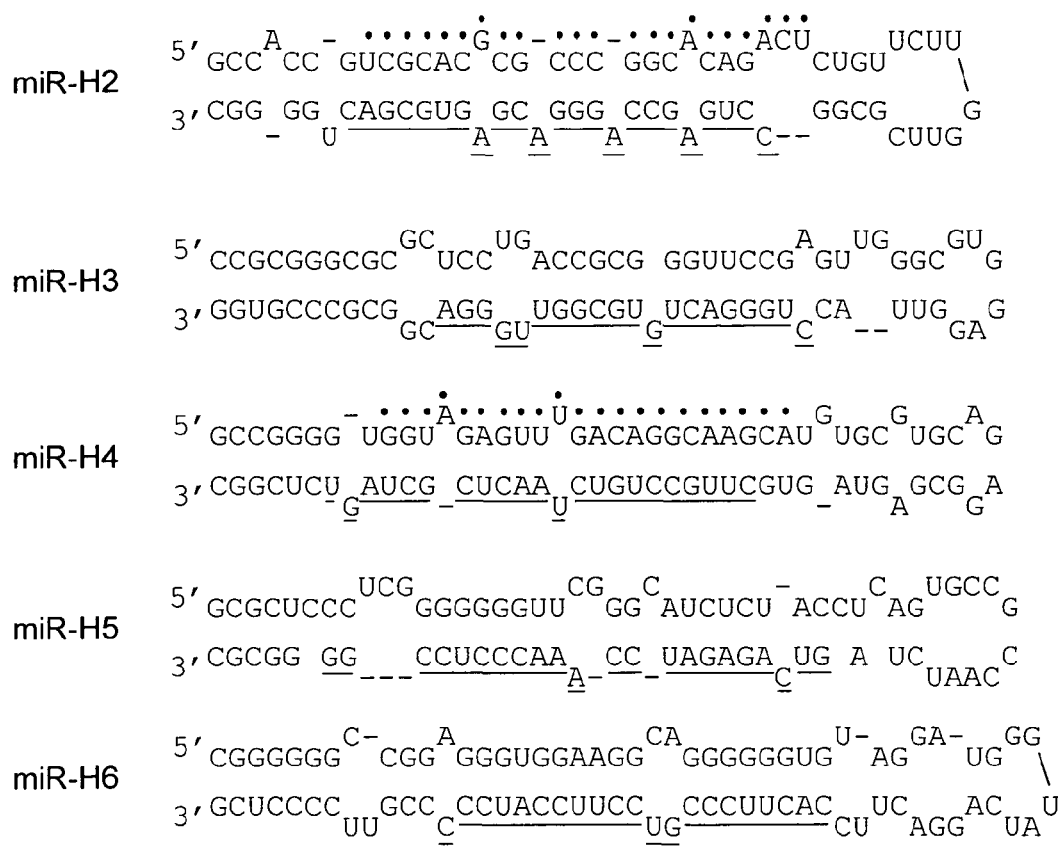
FIG. 2. Schematic of the predicted primary miRNA stem-loop structures for the viral miRNAs listed in Tables 1 and 2. The RNA stem-loop structures shown were predicted using mFOLD. The major miRNA products are shown in red (underlined sequences) and the passenger strands, where recovered, in blue (dotted sequences).

FIG. 9. Predicted secondary structures of the pri-miRNA hairpins for HSV-2 miR-H2 (SEQ ID NO: 21), HSV-2 miR-H3 (SEQ ID NO: 22), HSV-2 miR-H4 (SEQ ID NO: 23), HSV-2 miR-H5 (SEQ ID NO: 24) and HSV-2 miR-H6 (SEQ ID NO: 25). These hairpin structures were computer predicted as described in FIG. 2 and FIG. 4. Mature miRNAs are shown in red (underlined) and passenger strands in blue (dotted). The sequences of the mature HSV-2 miRNAs are further described in Table 10.

Figure 10:
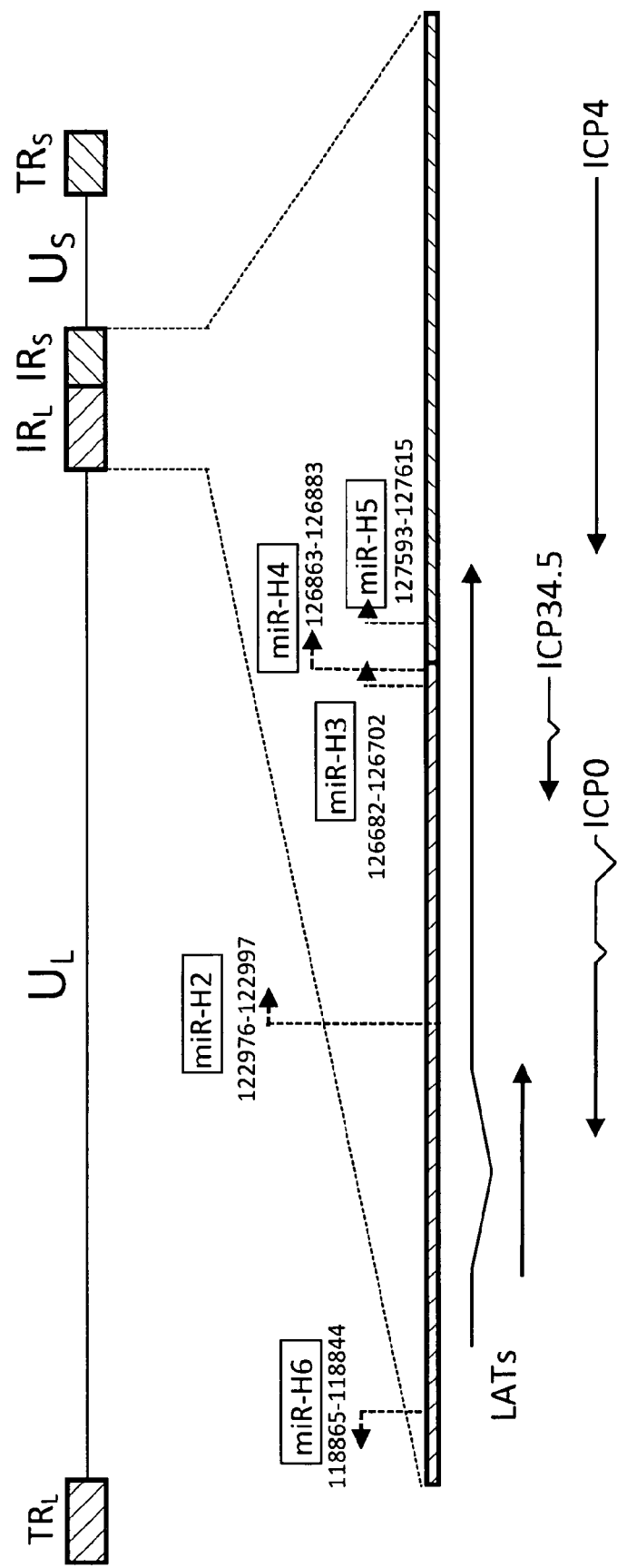

FIG. 10. Schematic of the HSV-2 genome showing details of the LAT locus. Relative sizes, locations and orientations of viral transcripts in the region are indicated. Sequence coordinates are given according to HSV-2 strain HG52 (NC_001798). Viral miRNAs miR-H2, -H3, -H4 and -H5 are in the same orientation as LAT, and miR-H6 is encoded in the opposite transcriptional orientation.

DETAILED DESCRIPTION OF THE INVENTION

Viral microRNAs have recently emerged as potentially key regulators of viral replication and pathogenesis in humans. As described below, deep sequencing has been used to identify a series of HSV-1- and HSV-2-encoded miRNAs that are expressed in latently HSV-1- or HSV-2-infected trigeminal ganglia and/or in cultured cells. Evidence indicates that these miRNAs are regulators of the ability of the virus to maintain a latent infection in humans. Agents that block the function of such miRNAs represent novel chemotherapeutic agents with the potential to cure latent viral infections in vivo. The present invention is described in detail below with reference to HSV-1 and HSV-2

The present invention relates, in a first embodiment, to virally encoded mature miRNAs and to the pri-miRNAs and pre-miRNA stem loop structures. In a second embodiment, the invention relates to agents that block the action of these virally encoded miRNAs and to methods of identifying same. In a further embodiment, the invention relates to methods of treating virus-infected individuals using such agents.

As noted above, the present invention relates to virus encoded miRNAs and to pri-miRNAs and pre-miRNA stem loop structures. Preferred miRNAs are HSV-1- or HSV-2-encoded miRNAs, particularly those expressed during latent infection in humans. Examples of HSV-1 encoded miRNAs of the invention include those set forth in Tables 1, 2, 6, 7, and 9. Examples of HSV-1 pri-miRNA and pre-miRNA stem-loop structures include those presented in FIGS. 2 and 4 (see also FIG. 3A). Examples of HSV-2-encoded miRNAs are set forth in Table 10. Examples of HSV-2 pri-miRNA and pre-miRNA stein-loop structures are given in FIG. 9. The invention also includes nucleic acids encoding an miRNA, a pri-miRNA or a pre-miRNA of the invention. The nucleic acid can be present in a vector (e.g., an expression vector) operably linked to a promoter.

In another embodiment, the invention relates to agents that block the function of the above-described viral encoded miRNAs. Suitable agents include antisense oligonucleotide agents, such as antagomirs, that have been shown to function effectively in vivo and in culture as specific inhibitors of individual miRNAs and pre-miRNAs (see, for example Published U.S. Application No. 20070213292; Gottwein et al, Nature 450:1096-1099 (2007); Krützfeldt et al, Nature 438: 685-689 (2005), Krützfeldt et al, Nucleic Acids Research 135:2885-2892 (2007)).

Suitable antagomirs include single-stranded, double-stranded, partially double-stranded or hairpin structured chemically modified oligonucleotides (DNA or RNA) that can include, for example, at least about 12 contiguous nucleotides complementary to, or substantially complementary to (that is, sufficiently complementary that a duplex can be formed), an HSV-1 or HSV-2-encoded miRNA. Preferably, the antagomir includes 12 or more contiguous nucleotides complementary to or substantially complementary to a target sequence of an miRNA or pre-miRNA nucleotide sequence. The length of the antagomir can contribute to the biochemical function of the antagomir with respect to the ability to decrease expression levels of a specific miRNA. An antagomir can be, for example, from about 12 to 30 nucleotides in length, preferably about 15 to 28 nucleotides in length (e.g., 16, 17, 18, 19, 20, 21, 22, 23, 24, 25, 26, or 27 nucleotides in length). In some instances, antagomirs can require at least 19 nucleotides in length for optimal function.

An antagomir of the invention can be further stabilized against nucleolytic degradation such as by the incorporation of a modification, e.g., a nucleotide modification. In one embodiment, the antagomir can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). In a preferred embodiment, the antagomir can include at least one 2'-O-methyl-modified nucleotide. In yet another preferred embodiment, the antagomir can include phosphorothioate backbone modifications. Antagomirs of the invention can be further modified so as to be attached to a ligand that is selected to improve stability, distribution or cellular uptake.

Other antisense oligonucleotides suitable for use in blocking, for example, HSV-1 expression include locked nucleic acids (Orom et al, Gene 372:137-141 (2006); Elmér et al, Nature 452:896-900 (2008)) and morpholinos (Kloosterman et al, PLoS Biol. 5:pe203 (2007)). One skilled in the art will appreciate that the availability of the sequences of the miRNAs immediately provides the sequences of suitable antisense oligonucleotide agents.

The invention further includes methods of identifying agents that can be used to block the function of the above-described viral encoded miRNAs. Candidate blocking agents include oligonucleotides as well as other types of molecules, including small molecules. Such methods can include, for example, binding assays, wherein an miRNA is contacted with a test compound and the presence or absence of a complex comprising the test compound and the miRNA is determined. The presence of a complex can indicate that the test compound is a candidate miRNA blocking agent. Test compounds can also be screened for their ability to block miRNA function, including, but not limited to, the ability of the viral miRNA to regulate viral replication. Assays that can be used to measure the function of miRNAs, including viral miRNAs, have been previously described (see, for example, Zeng et al, Mol. Cell 9:1327-1333 (2002); Gottwein et al, Cell Host Microbe. 3(6):375-87 (2008); Nature 450(7172):1096-9 (2007)).

The invention also includes compositions comprising the inhibitor (e.g., antagomirs) and a carrier. Such compositions can be formulated using standard techniques (see, for example, Published U.S. Application No, 20070213292). In one embodiment, the composition is a sterile injectable solution.

In a further embodiment, the invention relates to a method of treating a viral infection in a patient in need of such treatment. Such methods include curing latent infections in patients as well as treating symptoms of virus reactivations. In a specific aspect of this embodiment, the invention relates to a method of curing (treating) latent HSV-1 or HSV-2 infections, for example, from trigeminal or sacral ganglia. Latent infections (e.g., HSV-1 or HSV-2 infections) in humans can be cured or cleared by releasing the virus from latency by treatment with, for example, antisense reagents specific for the viral (e.g., HSV-1 or HSV-2) miRNAs (e.g., antagomirs), for example, while treating the patient with an anti-viral drug that targets replicating (but not latent) virus. Suitable antiviral drugs are well known in the art. Appropriate dosing regiments can vary with the individual, the nature of the viral infection and the agent used to block miRNA function. Preferred modes of administration include intravenous injection. Optimum regimens can be determined by one skilled in the art without undue experimentation.

Certain aspects of the invention can be described in greater detail in the non-limiting Examples that follows. (See also Pfeffer et al, Nat. Methods 2:269-276 (2005); Cui et al, J. Virol. 80:5499-5508 (2006); Gupta et al, Nature 442:82-85 (2006), Tang et al, Proc. Natl. Acad. Sci. 105:10931-10936 (2009), Tang et al, J. Viral. 83:1433-1442 (2009), Epub 2008 Nov. 19).

EXAMPLE 1

Experimental Details

Cells, viruses and RNA. 293T cells were maintained in DMEM supplemented with 10% FBS. SY5Y cells were maintained in RPMI also supplemented with 10% FBS. Total RNA for 454 sequencing, Northern blots, and splint-ligation assays was harvested using Trizol (Invitrogen). Vero cells were maintained in DMEM supplemented with 5% FBS. HSV-1 strain KOS and HSV-2 strain 186syn[+]-1 thymidine kinase-negative mutant, ΔKpn TK− (Jones et al, Virology 278:137-150 (2000)) were propagated and assayed essentially as described (Coen et al, J. Virol. 53:477-488 (1985)).

*Plasmid constructs, siRNAs and transfections.* pcDNA3/LAT was derived from an EcoRI-BamHI digest of pSG28 (Goldin et al, J. Virol. 38:50-58 (1981)), which released adjacent EcoRI-BamHI and BamHI-BamHI fragments. Together, the fragments contained the entire ~8.3 kb LAT as well as an additional ~130 bp upstream of the TATA box, and ~2.3 kb downstream of the polyadenylation signal. The two fragments were ligated into pcDNA3.1(−)/Zeo (Invitrogen) and screened to verify that the BamHI-BamHI fragment was oriented correctly. Transfection of pcDNA3/LAT into 293T cells was performed using FuGene (Roche), according to the manufacturer's instructions.

The ICP0 and ICP4 expression constructs pRS-1 and pSG28 K/B, respectively, were gifts from Dr. Roz Sandri-Goldin (Sekulovich et al, J. Virol. 62:4510-4522 (1988)). pRS-1 contains a 4.8 kb SstI-HpaI fragment from the HSV-1 genome, which encodes the entire ICP0 gene, including the cognate promoter and poly(A) site, inserted into SstI-SmaI sites in pUC18. pSG28 K/B contains a 9.0 kb BglII-KpnI fragment of the HSV-1 genome, which encodes the entire ICP4 gene, including the cognate promoter and poly(A) site, inserted into pUC18. The ICP0 riboprobe used for Northern blot analysis was generated by in vitro transcription of a linearized pcDNA3.1(−)/Zeo vector that contained a 431 bp BamHI-XhoI fragment of ICP0 cloned in the reverse orientation. The HA-tagged β-arrestin expression plasmid has been described (Wiegand et al, Embo J. 23:2451-2458 (2004)).

siRNAs designed to mimic the miR-H2-3p and miR-H6 duplex intermediates, and a mutant form of miR-H2-3p with 3 mutations (3M) in the seed region, were obtained from IDT. miR-H2-3p duplex 5' arm: 5'-UCGCACUCGUCCCUG-GCUCAGACU-3' (SEQ ID NO: 4); miR-H2-3p duplex 3' arm: CCUGAGCCAGGGACGAGUGCGACU-3' (SEQ ID NO: 5); miR-H2-3p-3M duplex 5' arm: 5'-UCG-CACUCGUCCCUGACGCAAACU-3' (SEQ ID NO: 6); miR-H2-3p-3M duplex 3' arm: 5'-CUUGCGUCAGGGAC-GAGUGCGACU-3' (SEQ ID NO: 7); miR-H6 duplex 5' arm: CACUUCCCGUCCUUCCAUCCC (SEQ ID NO: 8); miR-H6 duplex 3' arm: GAUGGAAGGACGGGAAGUAUA (SEQ ID NO: 9). All plasmid DNA and siRNA cotransfections were performed in 293T cells using Lipofectamine 2000 (Invitrogen), according to the manufacturer's directions. Briefly, 293T cells were plated the day before in 24-well plates to be 80-90% confluent day of transfection. Cells were co-transfected with either 60-80 ng of pRS-1 or 40-60 ng of pSG28 K/B, 30 ng of pβarr-HA, and 10 pmol of the appropriate siRNA duplex. One microliter of Lipofectamine 2000 was used per well per transfection. Samples were transfected in duplicate and harvested simultaneously ~24 hrs post-transfection-one sample was harvested for Western blot analysis and the other for RNA analysis.

Deep sequencing. Sample preparation for 454 sequencing was conducted as previously described (Hafner et al, Methods 44:3-12 (2008)), up to and including the RT-PCR step. After that point, the protocol as outlined by the Hannon laboratory on the 454 website (www.454.com) was followed. Initially, ~750 µg of total RNA from pcDNA3/LAT transfected 293T cells, and ~60 µg of total RNA isolated from latently HSV-1- or HSV-2-infected mouse trigeminal ganglia or HSV-1+ human trigeminal ganglia, was used. Sequence data analysis was performed using Microsoft Excel.

Samples were prepared for Solexa/Illumina deep sequencing using the Solexa Digital Gene Expression kit, but in some cases with 5' and 3' linkers custom ordered and modified from IDT. Samples were sequenced using a Genome Analyzer sequencing system (Illumina), and resulting sequence files were parsed and binned using a custom Ruby script. Data analysis was performed using Microsoft Excel and NCBI BLAST or SOAP (Li et al, Bioinformatics 24:713-714 (2008)). Potential miRNAs were further tested by MFOLD for their potential to form RNA hairpins (Zuker, Nucleic Acids Res 31:3406-3415 (2003)).

Northern blots and splint ligation assay. For the ICP0 Northern blot, 5 µg of total RNA was separated on a 0.6% agarose gel and transferred onto nitrocellulose. Membranes were fixed by UV irradiation and probed with an ICP0 riboprobe according to standard protocols. Bands were visualized by exposing blots to film at −80° C. overnight with intensifying screens. The LAT intron was detected by Northern blot using an oligononucleotide probe. Splint-ligation assays (USB) were performed with 12 µg of total RNA per sample, according to the manufacturer's directions.

Western blots. Samples were harvested and run out on 10% Tris-HCl gels (Bio-Rad), which were then transferred onto nitrocellulose. Blots were cut in half at the 72 kDa marker band so that the half with the larger proteins could be probed with mouse monoclonal antibodies specific for ICP0 or ICP4 (Virusys) and the half with the smaller proteins could be probed with an anti-HA monoclonal (Covance). Both halves were then incubated with anti-mouse secondary antibody (GE Healthcare) and bands visualized with Lumi-Light Western Blotting Substrate (Roche), according to the manufacturer's directions.

Latent HSV infection in mice. Procedures involving mice were approved by the Harvard Medical School Institutional Animal Care and Use Committee in accordance with federal guidelines. Male CD-1 mice were infected or mock infected with HSV-1 strain KOS as previously described (Leib et al, J. Virol. 63:759-768 (1989)) or with HSV-2 strain 186syn$^+$-1 thymidine kinase-negative mutant, ΔKpn TK− as previously described (Jones et al, Virology 278:137-150 (2000)), housed for 30 days, and then sacrificed for tissue harvest as previously described (Leib et al, J. Virol. 63:759-768 (1989)).

Human samples. Human trigeminal ganglia were obtained post-mortem and were provided on an anonymous basis. Small RNAs were isolated from excised trigeminal ganglia as described above.

Stem-loop RT PCR. Low molecular weight-enriched RNA was isolated with the mirVana miRNA Isolation Kit (Ambion) and the <40 nucleotide-length fraction isolated using the flashPAGE™ Fractionator System (Ambion). The equivalent of 2.1 µg of total RNA was amplified per reaction. Real time quantitative RT-PCR assays were designed for each miRNA with specific stem-loop transcription primers and PCR reagents, as described (Chen et al, Nucleic Acids Res. 33:e179 (2005)). RNA standards, stem-loop RT primers, and PCR primers were purchased from IDT, and TaqMan probes were purchased from Applied Biosystems, Inc (Foster City, Calif.) (Table 4B). Briefly, RNA was reverse is transcribed in duplicate with Multiscribe (Ambion) and miRNA-specific RT primers. Negative controls included reverse transcriptase-negative, RI primer-negative, and mock-infected experimental samples. Synthetic standard miRNAs were serially diluted and the dynamic range of each assay exceeded 5 orders of magnitude. Aliquots of cDNA were assayed on a PRISM 7700 Sequence Detection System (Applied Biosystems, Inc.). The detection limit was defined by the threshold cycle (Ct) of the negative controls.

Results

In latently infected neurons, HSV-1 expresses only one abundant transcript, the ~8.3 kb capped, polyadenylated LAT (FIG. 1A) (Bloom, Int. Rev, Immunol. 23:187-198 (2004), Stevens et al, Science 235:1056-1059 (1987)). LAT is spliced to give an ~2.0 kb stable intron and a predicted unstable ~6.3 kb exonic RNA (Farrell et al. Proc. Natl. Acad. Sci. USA 88:790-794 (1991), Kang et al, Virology 356:106-114 (2006)). As LAT is not generally thought to encode a protein, it was hypothesized that the exonic, regions of LAT might function as a primary miRNA precursor. To identify HSV-1

Figures 1A, 1B:
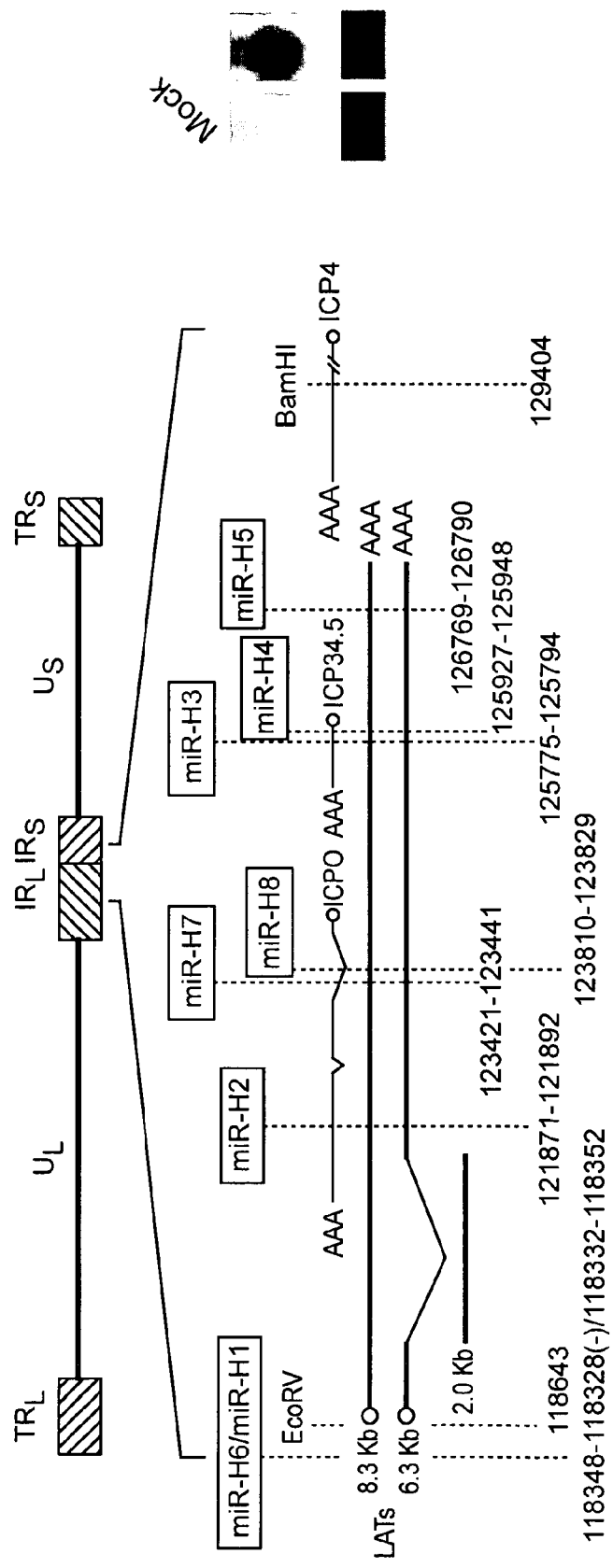
FIGS. 1A and 1B. Genomic location of HSV-1 miRNAs.

LAT-derived miRNAs, a LAT expression plasmid, pcDNA3/LAT, was constructed in which a heterologous promoter drives transcription of an ~10.8 kb HSV-1 genomic restriction fragment containing the entire 8.3 kb LAT gene (FIG. 1A). This plasmid was transfected into human 293T cells and total RNA was isolated. Northern analysis revealed high level expression of the stable LAT intron (FIG. 1B).

Small RNAs derived from this sample were used to prepare cDNAs for 454 sequencing (Hafner et al, Methods 44:3-12 (2008)). This resulted in 225,439 sequence reads, of which 185,204 represented cDNAs recovered two or more times (Table 3). Of these, at least 144,955 represented cellular miRNAs, while 619 were HSV-1-derived miRNAs (Tables 1 and 3). Six distinct HSV-1 miRNA sequences were obtained, which derived from four different HSV-1 miRNA precursor hairpins (FIG. 3A). The two most common HSV-1 miRNAs cloned were miR-H2-3p (265 reads) and miR-H4-3p (266 reads) and those derived from miRNA stem-loops that also gave rise to passenger strands miR-H2-5p (10 reads) and miR-H4-5p (61 reads) (FIG. 3A). miR-H3 (5 reads) and miR-H5 (40 reads) were also cloned. For each miRNA, HSV-1 LAT could be folded into the expected precursor stem-loop structure (FIG. 3A). Where both the miRNA and passenger strand were recovered, the characteristic ~2 nt 3' overhangs were observed in the duplex intermediate (FIG. 3A).

These data show that LAT can be processed into miRNAs in culture but do not address expression in vivo. Small RNAs were, therefore, isolated from trigeminal ganglia of mice latently infected with HSV-1 and deep sequencing of derived cDNAs was performed. 254,651 sequence reads were obtained, of which 224,729 represented RNAs recovered two or more times (Table 3). Of these, 204,867 represent known cellular miRNA sequences while 144 represented HSV-1 miRNAs (Tables 2 and 3). While this number may seem low, it is noted that only ~10% of the cells in a trigeminal ganglion are neurons—the only cells latently infected by HSV-1—and that in a typical ganglion only a small fraction a of all neurons are infected (Sawtell, J. Virol. 71:5423-5431 (1997)). Assuming a neuronal infection rate of ~10%, only ~1% of all miRNAs from trigeminal ganglia could be HSV-1 derived, even if 100% of the miRNAs in infected cells were viral. In fact, data obtained using other herpesviruses suggest that viral miRNAs constitute a minority of miRNAs in latently infected cells (Cai et al, Proc. Natl. Acad. Sci. USA 102:5570-5575 (2005)).

Four distinct HSV-1 miRNAs were recovered from trigeminal ganglia (FIG. 3A, Table 2). miR-H2-3p (94 reads) and miR-H3 (18 reads) represent LAT-derived miRNAs previously identified in LAT-expressing 293T cells (FIG. 3A). However, a third HSV-1 miRNA cloned from infected trigeminal ganglia, miR-H6, is not of LAT origin. Instead, miR-H6 is derived from an RNA stem-loop encoded on the opposite strand of the HSV-1 genome and located within the LAT promoter (FIG. 1A). This sequence was not present in pcDNA3/LAT and, therefore, could not be detected in transfected 293T cells.

Figure 3B:
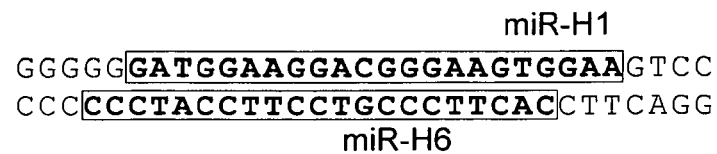

The identification of miR-H6 is striking for two reasons. Firstly, miR-H6 must derive from a second HSV-1 primary miRNA precursor, distinct from LAT, that is expressed in latently infected neurons. While a transcript antisense to the LAT promoter has previously been described (Perng et al, J. Virol, 76:8003-8010 (2002)), the reported ends of this transcript exclude miR-H6. The lack of any previous report of this primary miRNA precursor may reflect the fact that it must be cleaved to generate miR-H6, and hence is likely to be unstable. Secondly, the stein-loop that gives rise to miR-H6 is the mirror image of a stein-loop transcribed from the opposite DNA strand that gives rise to a previously described HSV-1 miRNA, miR-H1, expressed late in productive replication (FIG. 3A) (Cui et al, J. Virol. 80:5499-5508 (2006)). The phenomenon of distinct miRNAs derived by bidirectional transcription of a single genomic locus was recently described in Drosophila for miR-iab-8-5p and miR-iab-4-5p (Tyler et al, Genes Dev. 22:26-36 (2008), Stark et al, Genes Dev. 8-13 (2008), Bender, Genes Dev. 22:14-19 (2008)). However, unlike these two insect miRNAs, which are similar in sequence, miR-H1 and miR-H6 are complementary (FIG. 3B).

Figure 3C:
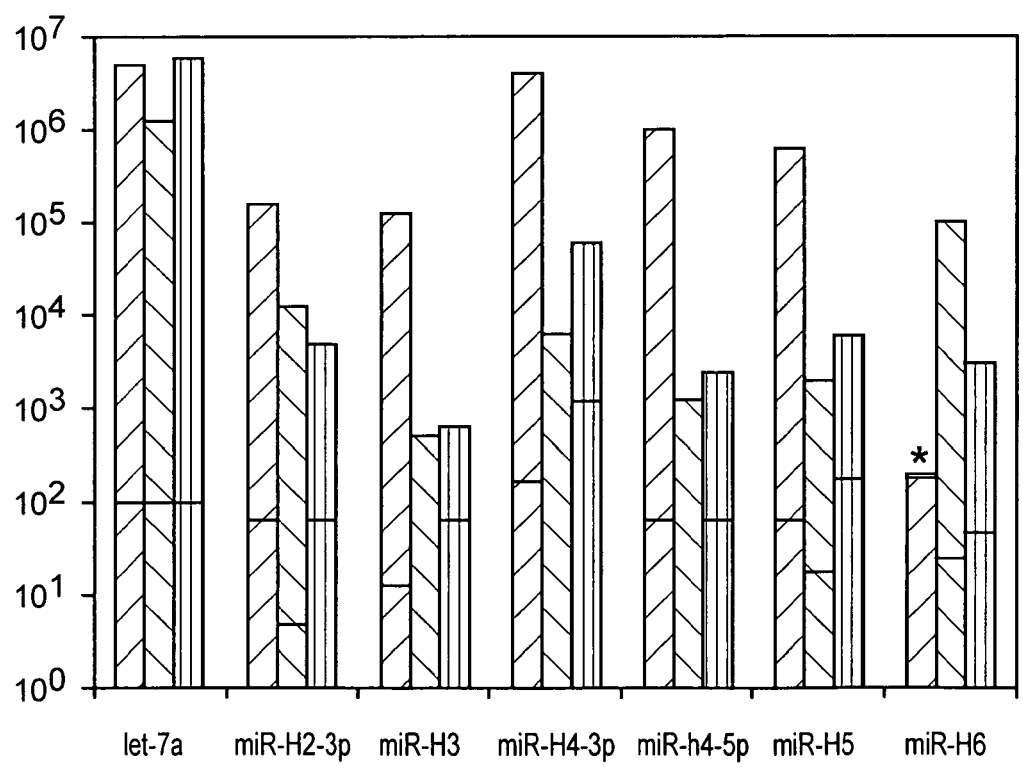
Figure 4:
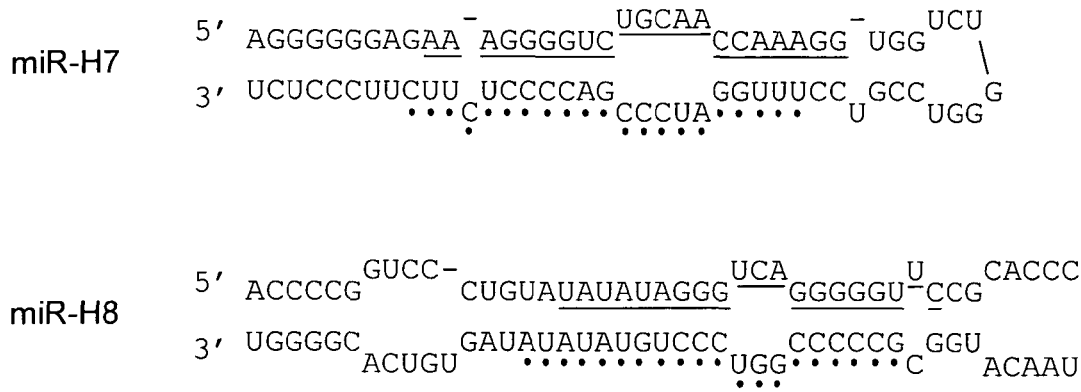
FIG. 4. Schematic of the predicted primary stem-loop structures for two HSV-1 miRNAs identified in human patients. Similar to FIG. 2, except that these HSV-1 miRNAs were detected in HSV-1 infected human trigeminal ganglia (Tables 6 and 7). The mature miRNA is shown in red (underlined) and the passenger strand in blue (dotted). The designation as passenger strand does not preclude incorporation into RISC, and function as a miRNA, for both the miR-H7 (SEQ ID NO: 17) and miR-H8 (SEQ ID NO: 18) passenger strands and the other passenger strands identified herein.

The data presented in FIG. 3 were derived either from transfected cells or from mice. To extend these data to human samples, Solexa/Illumina deep sequencing of two HSV-1 positive human trigeminal ganglia, obtained post-mortem, was performed. For patient 1, a total of 9,152,800 DNA reads were obtained and, for patient 2, 3,086,881 total DNA reads were obtained. In other words, this technology made it possible to obtain >3×10$^6$ individual short RNA sequences from each of these primary tissue samples. This is important as HSV-1 is expected to infect a very small percentage of cells in the human trigeminal ganglia and is, therefore, expected to contribute <0.1% of all the miRNA sequences obtained. Consistent with this expectation, the analysis revealed a total of 2,952 individual reads of HSV-1 origin in patient 1 and 262 reads in patient 2 (Table 5). Most of these miRNAs are identical to the HSV-1 miRNAs previously identified in latently HSV-1-infected mouse trigeminal ganglia (Tables 1 and 2). However, two novel HSV-1 miRNAs were identified, miR-H7 and miR-H8 (Tables 6, and 7, FIG. 4). miR-H7 was identified in both patients, and both the miRNA and the passenger strand were detected. Although miR-H8 was only identified in one patient, both pre-miRNA strands were again obtained (Table 5). The sequences of the miRNA and passenger strands, and of the predicted pri-miRNA precursor, are shown in FIG. 4. It is currently unclear why the HSV-1 miR-H7 and miR-H8 miRNAs were not detected in murine trigeminal ganglia but it is possible that this is due to differences in miRNA processing efficiency between those mice and human neurons As the sequencing data shown in Tables 6 and 7, obtained by Solexa/Illumina sequencing of small RNAs derived from HSV-1 positive human trigeminal ganglia, identified significantly more HSV-1 miRNAs than had been observed in the mouse trigeminal ganglia analyzed in Table 2 using 454 sequencing, the analysis of the mouse trigeminal ganglia samples was repeated using this alternative deep sequencing technique and using a newly derived RNA sample. Broadly speaking, these data (Table 8) revealed no novel miRNAs that were not previously identified, with the exception that nine individual cDNAs encoding HSV-1 miR-H1 were recovered (Table 9). It is important to note that the actual recovered sequence of the mature HSV-1 miR-H1 miRNA shown here in fact differs from that predicted previously at both the 5' and 3' ends (Cui et al., J. Virol. 80: 5499-5508 (2006)). In addition, Solexa/Illumina deep sequencing of small RNAs derived from latently HSV-1-infected murine trigeminal ganglia also detected miR-H7-5p and miR-H8-5p at low frequencies (Table 8). Moreover, a substantial number of miR-H3-3p sequences (78) were recovered. Also recovered was a single example of the miR-H3-5p passenger strand and a substantial number (126) of hits derived from the mature miR-H4-5p miRNA and a smaller number (11) of hits derived from miR-H4-3p. The higher level of expression of miR-H4-5p seen in the murine sequencing experiment agrees with the results obtained in humans (Table 5) but disagrees with the data obtained in transfected 293T cells (FIG. 3A), where miR-H4-

3p was predominant. It is, therefore, currently unclear which of these two miR-H4-derived miRNAs can be viewed as the primary product and, indeed, both miR-H4-derived miRNAs may be actively incorporated into RISC. Finally, these data also recovered the miR-H5-5p and miR-H6-5p passenger strands for the first time (Table 8). Together, these data show that there are at least 8 pri-miRNA stem-loops located in the HSV-1 genome that are processed into mature miRNAs in latently HSV-1-infected human neurons in vivo.

To ascertain whether any of these HSV-1 miRNAs were expressed during productive HSV-1 infection, where LAT is expressed late in infection (Kang et al, Virology 356:106-114 (2006)), quantitative stem-loop RT-PCR was performed for miR-H1 through miR-H6 using RNA preparations derived from HSV-1 infected Vero cells (FIG. 3C and Table 4), All six HSV-1 miRNAs were, in fact, present in infected Vero cells. The two "non-LAT" HSV-1 miRNAs, miR-H1 and miR-H6, were each detected at >$10^5$ molecules per 2.1 µg of total RNA, while the four LAT-derived miRNAs were detected at between $4 \times 10^2$ (miR-H3) and $4 \times 10^3$ (miR-H4-3p) molecules (FIG. 3C). These data confirm that these six HSV-1 miRNAs are indeed expressed in productively infected cells, albeit at low levels in the case of the four LAT-derived miRNAs.

RT-PCR analysis of pcDNA3/LAT transfected 293T cells (FIG. 3C) also detected four LAT-derived miRNAs but, as expected, did not detect miR-H6, which is not present in this vector (miR-H1 was not analyzed). With the exception of miR-H2-3p, which was captured at an unusually high efficiency by cDNA sequencing, there was a good correlation of LAT miRNA expression levels in 293T cells as determined either by sequencing or RT-PCR (FIGS. 3A and 3C). Additionally, RT-PCR analysis of short RNAs derived from mouse trigeminal ganglia demonstrated the expression of these four LAT-derived HSV-1 miRNAs, as well as miR-H6 (FIG. 3C and Table 4). miR-H1, which is primarily expressed late during HSV-1 replication (Cui et al, J. Virol. 80:5499-5508 (2006)), was not detected in latently infected mouse ganglia in this experiment and may be expressed below the level of detection sensitivity.

Figure 5:
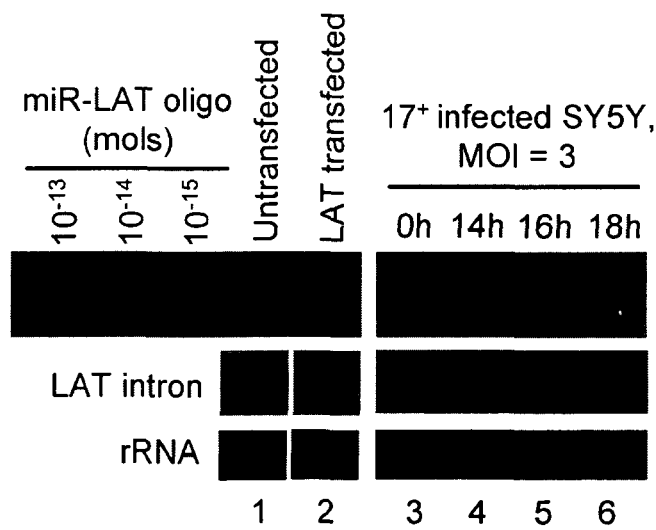
FIG. 5. The proposed miR-LAT miRNA is not detected in HSV-1 infected cells. Using splint-ligation, miR-LAT was not detected in SY5 cells infected with HSV-1 strain 17syn+, (lanes 4 to 6) or in 293 T cells transfected with pcDNA3/LAT (lane 2). In contrast, the LAT intron, and a synthetic RNA identical to miR-LAT, were readily detected, in the latter case at a level equivalent to ~300 copies per cell.
Figure 7:
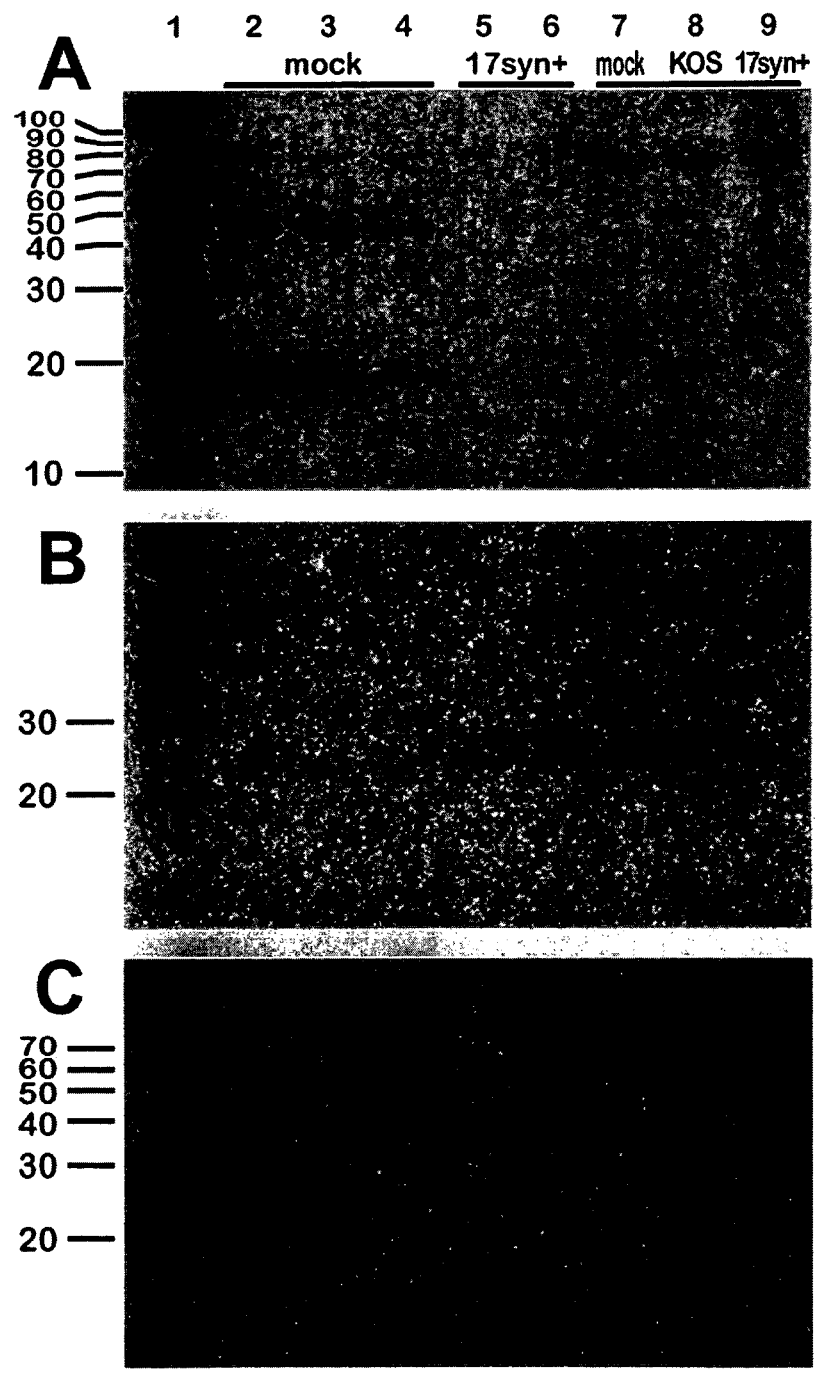
FIGS. 7A-7C. Northern blot analysis detects synthetic, but not endogenous, miR-LAT. HSV- or mock-infected SY5Y cells were harvested at 16 hr P.I., the time reported by Gupta et al (Nature 442:82-85 (2006)). Short-enriched RNA was isolated using the mirVana™miRNA Isolation Kit (Ambion, Inc.). $^{32}$P-end-labeled probes had specific activities of >1×10$^8$ cpm/pmol. Synthetic miR-LAT and pre-miR-LAT mimic (3, 1.5, and 0.75×10$^{10}$ molecules, lanes 2, 3, 4) were combined with cellular RNA.

Although it was possible to clone HSV-1 miRNAs from both LAT-expressing 293T cells and infected ganglia, the previously reported miR-LAT was not detected (Gupta et al, Nature 442:82-85 (2006)). miR-LAT was also not detected in SY5Y cells infected with the strain of HSV-1 used in the original report, using a sensitive splint-ligation assay (FIG. 5), RT-PCR (Table 4) or Northern analysis (FIG. 7), under conditions where a synthetic RNA identical to the reported miR-LAT sequence was readily detected. The report describing miR-LAT was recently retracted.

Figure 6:
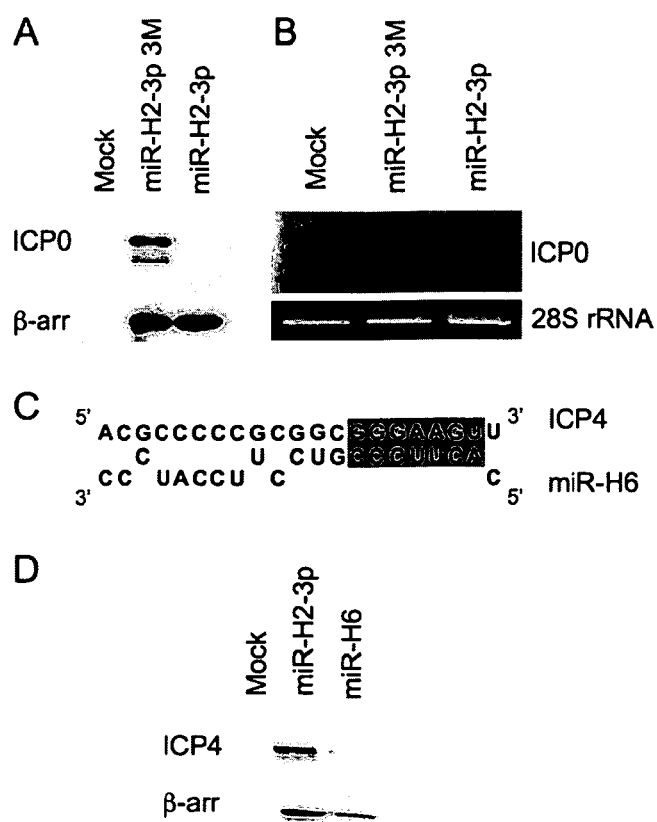
FIGS. 6A-6D. Downregulation of ICP0 and ICP4 protein expression by HSV-1 miRNAs.

Mapping of the eight HSV-1 miRNAs onto the HSV-1 genome reveals that miR-H2 is antisense to the ICP0 transcript, while both miR-H3 and miR-H4 are antisense to ICP34.5 (FIG. 1A). ICP0 is an HSV-1 transcriptional activator, expressed as an immediate-early gene; that has been proposed to play a key role in promoting viral replication and reactivation from latency (Everett, Bioessays 22:761-770 (2000); Cai et al, J. Virol. 67:7501-7512 (1993); Halford et al., J. Virol. 75:6143-6153 (2001)). To examine whether miR-H2-3p could affect ICP0 protein or mRNA expression, 293T cells were co-transfected with an ICP0 expression plasmid and an siRNA designed to mimic the miR-H2 miRNA duplex intermediate (FIG. 3A). As shown in FIG. 6, miR-H2-3p strongly inhibited the expression of ICP0 protein (FIG. 6A) but, unexpectedly, did not affect ICP0 mRNA expression (FIG. 6B). Therefore, despite the perfect homology of miR-H2-3p to ICP0 mRNA, inhibition of ICP0 protein expression by this viral miRNA occurs primarily at the translational level (Bartel, Cell 116:281-297 (2004)). These data are consistent with earlier reports suggesting that LAT reduces ICP0 protein, but not mRNA, levels (Thompson et al, J. Virol. 77:12319-12330 (2003), Mador et al, J. Virol. 72:5067-5075 (1998), Farrell et al, Proc. Natl. Acad. Sci, USA 88:790-794 (1991), Chen et al, J. Virol. 4764-4772 (2002)).

Analysis of the sequence homology of the HSV-1 miRNAs to other HSV-1 genes revealed homology between miR-H6, including the miRNA seed region (Bartel, Cell 116:281-297 (2004)) and the mRNA encoding ICP4, a transcription factor required for expression of most HSV-1 genes during productive infection (FIG. 6C) (Preston, J. Virol. 29:275-284 (1979)). Co-transfection of an ICP4 expression plasmid with a synthetic form of the predicted miR-H6 duplex intermediate revealed strong downregulation of ICP4 protein expression (FIG. 6D).

Thus, described above are eight novel HSV-1 miRNAs, four of which have previously been computationally predicted (Cui et al, J. Virol, 80:5499-5508 (2006), Pfeffer et al, Nat. Methods 2:269-276 (2005)). Six of these viral miRNAs derive from the second exon of the predicted spliced ~6.3 kb LAT (FIG. 1A) and these miRNAs may provide both a rationale for the existence of spliced LAT and explain its characteristic instability (Bloom, Int. Rev. Immunol. 23:187-198 (2004); Kang et al, Virology 356:106-114 (2006)), i.e. LAT is likely degraded in is the nucleus due to Drosha cleavage (Bartel, Cell 116:281-297 (2004)). In addition to the six LAT-derived HSV-1 miRNAs, a seventh miRNA was also identified, miR-H6, derived from a currently unknown primary miRNA precursor that lies antisense to the LAT promoter and that must also be expressed in latently infected neurons (FIG. 1A). Of interest, miR-H6 is antisense to a previously predicted late HSV-1 miRNA, miR-H1 that was also sequenced here for the first time (Table 9, FIG. 3) (Cui et al, J. Virol. 80:5499-5508 (2006)). However, miR-H6 is expressed independently of miR-H1.

Three of the latently expressed HSV-1 miRNAs are transcribed antisense to HSV-1 mRNAs—ICP0 mRNA in the case of miR-H2-3p and ICP34.5 mRNA in the case of both miR-H3 and miR-H4-3p (FIG. 1A)—and it has been demonstrated that miR-H2-3p is indeed able to inhibit ICP0 protein expression (FIG. 6A). As ICP0 is a key immediate-early HSV-1 transcriptional activator thought to promote entry into the productive replication cycle (Everett, Bioessays 22:761-770 (2000); Cai et al, J. Virol. 67:7501-7512 (1993), Halford et al, J. Virol. 75:6143-6153 (2001)), inhibition of ICP0 expression by miR-H2-3p may increase the likelihood that neurons become and remain latently infected. It has in fact been previously proposed that. LAT inhibits ICP0 expression post-transcriptionally in neurons (Stevens et al, Science 235: 1056-1059 (1987); Thompson et al. J. Virol. 77:12319-12330 (2003); Farrell et al, Proc. Nati. Acad, Sci. USA 88:790-794 (1991)) and the existence of miR-H2-3p could explain this phenomenon. It was also observed that miR-H6 displays partial homology to ICP4 mRNA, including the entire miRNA seed region (Bartel, Cell 116:281-297 (2004)), and can reduce ICP4 protein expression (FIGS. 6C and 6D), Like ICP0, ICP4 can promote exit from latency (Halford et al, J. Virol. 75:6143-6153 (2001)), and inhibition of ICP4 expression may therefore enhance the robustness of the latent state.

Figure 8:
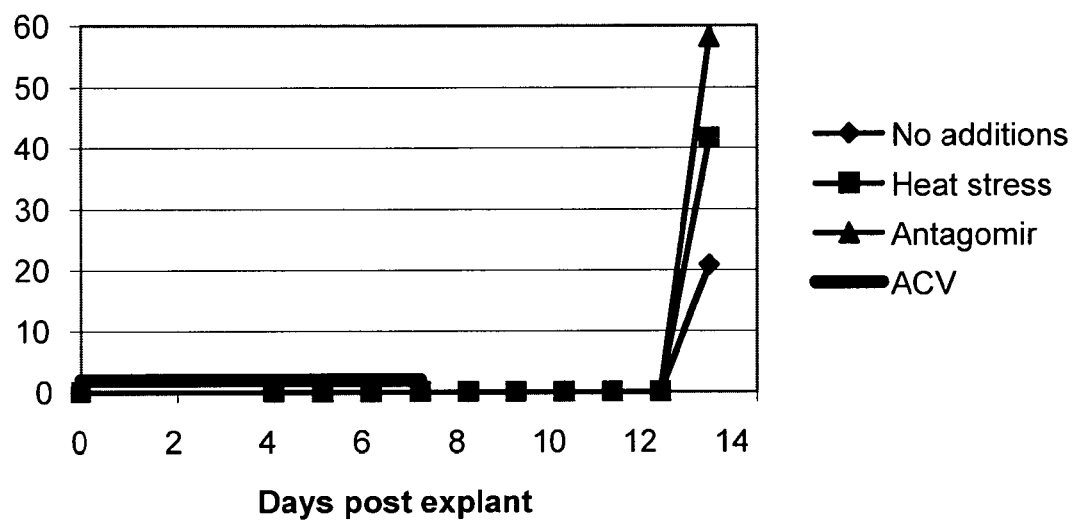
FIG. 8. Antagomirs specific for the HSV-1 miRNAs miR-H2-3p and miR-H6 and re-activation of HSV-1 from latently infected neurons in culture. Latently HSV-1-infected trigeminal ganglia were excised from mice and cultured in the presence of acyclovir (ACV) for the time indicated (purple bar). The ACV was then removed. On day 12 of culture, the cultures were either mock-treated (no additions, in blue), in the presence of heat stress (in red), or in the presence of anti-H2-3p and anti-H6 antagomirs in green). The Antagomirs used were antisense to the entire length of the most common variants of miR-H2-3p and miR-H6 and are 24nt and 21nt, respectively.

To test whether inhibiting HSV-1 miR-H2-3p and miR-H6 in latently infected cells with antisense oligonucleotides such as antagomirs would indeed to lead to reactivation, primary cultures of trigeminal ganglion cells were prepared from mice that had been infected 30 days previous with HSV-1. The cultures were prepared in the presence of nerve growth factor (NOF) and acyclovir, as described (Halford et al., J. Virol. 70: 5051-5060 (1996)). After one week, the acyclovir was removed and cultures were maintained five more days with no is evidence of infectious virus (see FIG. 8). At that time, for each of three 24-well plates, the medium was replaced with medium lacking NGF and left at 37° C. (no additions); replaced with that medium, incubated for 3 hrs. at 43° C., then returned to 37° C. (heat stress), a stimulus known to induce reactivation; or replaced with that medium containing 200 nM each anti-miR-H2 and anti-miR-H6 antagomirs and incubated at 37° C. (antagomir). Twenty-four hours later, each well was scored for cytopathic effect. The antagomir-treated cultures showed ~3-fold more reactivation than the no additions control, and even more reactivation than the heat-stressed cultures (see FIG. 8). These data suggest that inhibition of viral miRNA function in latently HSV-1- or HSV-2-infected human neurons would also reactivate the latent virus.

While the effect of miR-H3 and miR-H4-3p on ICP34.5 expression has not been directly examined, it appears likely that these viral miRNAs are also acting as inhibitors of viral gene expression. Data favoring this hypothesis come from analysis of the L/ST transcripts that overlap the 3' end of LAT (FIG. 1A). LIST RNAs are expressed by HSV-1 mutants lacking ICP4 (Yeh & Schaffer, J. Viral. 67:7373-7382 (1993)), Importantly, the L/ST RNAs, which have the potential to give rise to miR-H3 and miR-H4-3p (FIG. 1A), are known to inhibit ICP34.5 expression via an "antisense" mechanism (Randall & Roizman, J. Virol. 71:7750-7757 (1997); Lee & Schaffer, J. Virol. 72:4250-4264 (1998)) and these viral miRNAs are presumably responsible for this effect. While inhibition of viral mRNA expression by cognate viral miRNAs has been previously reported (Pfeffer et al, Science 304:734-736 (2004); Sullivan et al, Nature 435:682-686 (2005); Grey et al, PLoS Pathog, 3:e163 (2007)), HSV-1 appears to use miRNA-mediated regulation of viral gene expression extensively to control entry into, and exit from, latency. Nevertheless, the existence of important cellular mRNA targets for HSV-1 miRNAs, especially miR-H1, miR-H5, miR-H7 and miR-H8 remains a strong possibility.

The results of the studies described above show that HSV-1 LAT functions as a pri-miRNA precursor that encodes six distinct miRNAs in HSV-1 infected cells. One of these miRNAs, miR-H2, is transcribed antisense to ICP0, a viral immediate-early transcriptional activator thought to play a key role in initiating productive HSV-1 replication and reactivation from latency (Everett, Bioessays 22:761-770 (2000)). While miR-H2 is indeed able to reduce ICP0 protein expression, miR-H2 does not affect ICP0 mRNA levels, despite this perfect complementarity, and, therefore, appears to inhibit ICP0 translation. A seventh HSV-1 miRNA was also identified in latently infected trigeminal ganglia, miR-H6, which derives from a previously unknown transcript distinct from LAT. miR-H6 displays complete seed homology to the mRNA encoding a second HSV-1 transcription factor, ICP4, and inhibits expression of ICP4, which is required for expression of most HSV-1 genes during productive infection (Preston, J. Virol. 29:275-284 (1979)). These results may explain the reported ability of LAT to promote latency (Thompson et al, J. Virol. 77:12319-12330 (2003); Mador et al, J. Virol. 72:5067-5075 (1998); Garber et al, J. Virol. 71:5885-5893 (1997); Chen et al, J. Virol. 71:5878-5884 (1997)). Thus, HSV-1 expresses several miRNAs in latently infected neurons that appear to facilitate the establishment and maintenance of viral latency by post-transcriptionally regulating viral gene expression.

EXAMPLE 2

To extend the analyses described above to the closely related virus HSV-2, deep sequencing was performed, using the Solexa/Illumina method, to identify re HSV-2-derived miRNAs in latently HSV-2-infected mouse trigeminal ganglia. In essence, this study was performed as described above for HSV-1 and comparable results were achieved, i.e., it was possible to identify five novel HSV-2 pre-miRNAs (FIG. 9) that gave rise to several mature HSV-2 miRNAs derived from either the 5' or 3' arm of the predicted pre-miRNA, as shown in Table 10 and summarized in Table 11. Strikingly, the five predominant HSV-2 miRNAs obtained showed extensive sequence homology, ranging from 60% to 77% sequence identity, to the HSV-1 miRNAs miR-H2-3p, miR-H3-3p, miR-H4-5p, miR-H5-5p and miR-H1-5p, as shown in Table 12. Moreover, these HSV-2 miRNAs are not only similar in sequence to their HSV-1 homologs, but are actually also encoded at the same location in the HSV-2 genome (compare FIG. 10 and FIG. 1). Specifically, HSV-2 miR-H2, like the very similar HSV-1 miR-H2, is located in HSV-2 LAT at a location, antisense to the ICP0 gene (FIG. 10), while HSV-2 miR-H3 and miR-H4, like HSV-1 miR-H3 and miR-H4, are located in HSV-2 LAT antisense to the ICP34.5 gene (FIG. 10). Finally, miR-H5 is located between the ICT4 and ICP34.5 genes in both HSV-1 and HSV-2. An exception arises in the case of HSV-2 miR-H6, which is located at the genomic location seen for HSV-1 miR-H6 but is more extensively homologous in sequence to miR-H1, which is encoded on the opposite DNA strand in the HSV-1 genome (FIG. 1) directly opposite HSV-1 miR-H6 (FIG. 3B), than it is to HSV-1 miR-H6 (Table 12).

In conclusion, five HSV-2 miRNAs have been identified that are very similar in sequence to five of the HSV-1 miRNAs described herein and that are also at the same genomic locations. These data are consistent with the hypothesis that these HSV-1 and HSV-2 miRNAs likely perform the same function in stabilizing viral latency in latently infected human ganglia. This is likely to include the specific downregulation of the viral ICP0, ICP4 and ICP34.5 genes.

Table 1 discloses SEQ ID NOS 26-56, respectively, in order or appearance. Table 2 discloses SEQ ID NOS 57-79, respectively, in order of appearance. Table 4B discloses SEQ ID NOS 80-112, respectively, in order of appearance. Table 6 discloses SEQ ID NOS 113-202, respectively, in order of appearance. Table 7 discloses SEQ ID NOS 203-222, respectively, in order of appearance. Table 9 discloses SEQ ID NOS 223-225, respectively, in order of appearance. Table 10 discloses SEQ ID NOS 226-256, respectively, in order of appearance. Table 12 discloses SEQ ID NOS 257-268, respectively, in order of appearance.

\* \* \*

All documents and other information sources cited above are hereby incorporated in their entirety by reference.

SEQUENCE LISTING

```
<160> NUMBER OF SEQ ID NOS: 268

<210> SEQ ID NO 1
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      probe

<400> SEQUENCE: 1 gggcccggg ccgggccgcc acg                                             23

<210> SEQ ID NO 2
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
agucgcacuc gucccuggcu cagg                                            24

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gggauggaag gacgggaagu g                                               21

<210> SEQ ID NO 4
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ucgcacucgu cccuggcuca gacu                                            24

<210> SEQ ID NO 5
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ccugagccag ggacgagugc gacu                                            24

<210> SEQ ID NO 6
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ucgcacucgu cccugacgca aacu                                            24

<210> SEQ ID NO 7
<211> LENGTH: 24
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 7
cuugcgucag ggacgagugc gacu                                              24

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
cacuucccgu ccuuccaucc c                                                 21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gauggaagga cgggaaguau a                                                 21

<210> SEQ ID NO 10
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
gccaccgucg cacgcgcccg gcacagacuc uguucuuggu ucgcggccug agccagggac       60
gagugcgacu ggggc                                                        75

<210> SEQ ID NO 11
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ccgcgggcgc gcuccugacc gcgdgguuccg aguugggcgu ggagguuacc ugggacugug      60
cgguugggac ggcgcccgug g                                                 81

<210> SEQ ID NO 12
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gccggggugg uagaguuuga caggcaagca ugugcgugca gaggcgagua gugcuugccu       60
gucuaacucg cuagucucgg c                                                 81
```

```
<210> SEQ ID NO 13
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gcgcucccuc gggggggguuc gggcaucucu accucagugc cgccaaucuc aggucagaga     60
uccaaacccu ccggggcgc                                                  80

<210> SEQ ID NO 14
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14 cgggggggccg gagggtuggaa ggcaggggggg uguaggaugg guaucaggac uuccacuucc    60
cguccuucca uccccccguuc cccucg                                         86

<210> SEQ ID NO 15
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
cgaggggaac gggggaugga aggacgggaa guggaagucc ugauacccau ccuacacccc     60
ccugccuucc acccuccggc cccccg                                          86

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16 gggggggatgg aaggacggga agtggaagtc c                                   31

<210> SEQ ID NO 17
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17 agggggggaga aagggucug caaccaaagg uggucugggu ccguccuuug gaucccgacc      60
ccucuucuuc ccucu                                                      75

<210> SEQ ID NO 18
<211> LENGTH: 87
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 18
accccggucc cuguauauau agggucaggg gguuccgcac cccuaacau ggcgccccg    60 gucccuguau auauaguguc acggggu                                      87

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
acgcccccgc ggcgggaagu u                                            21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
cacuucccgu ccuuccaucc c                                            21

<210> SEQ ID NO 21
<211> LENGTH: 93
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ucccgacccg cgcgcgucgg ucgcgccugc ccggcccaga cucugugcuu gggugucggu    60
cugagccugg gucaugcgcg accgggcgcg cgg                                 93

<210> SEQ ID NO 22
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ggccggcgcg cucucgaccg cgguucccga gucguacgca gggaccauuu gggagucugc    60
gguugggagc gcgccggggc                                                80

<210> SEQ ID NO 23
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ggagcgcguc ggggcgggag aguucacucg gcacgcaugc acguguaacc gccaguccgu    60
gcuugccuag cgaacucacc cgucccggcu ggcgug                              96

<210> SEQ ID NO 24
<211> LENGTH: 93
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
cuucccuccc gcuccugcgg gggggcucgg gccaccugac cuucguaacc ugcacucagg     60
ucagagcccc agaccccccg cgggcgcggg aga                                 93

<210> SEQ ID NO 25
<211> LENGTH: 114
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 25
gggcgucggg acucgcggag ggccggagaa uggaaggcga ggggaugcag gaggaggauc     60
gggacucccc aucuucugcc cuuccauccu ccguuuuucc gcuuuccacc gccg          114

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tcgcacgcgc ccggcacaga ct                                             22

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tcgcacgcgc ccggcacaga                                                20

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cctgagccag ggacgagtgc ga                                             22

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 29
cctgagccag ggacgagtgc gact                                          24

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cctgagccag ggacgagtgc gac                                           23

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cctgagccag ggacgagtgc g                                             21

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cctgagccag ggacgagtgc gaca                                          24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tgagccaggg acgagtgcga ctga                                          24

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tgagccaggg acgagtgcga                                               20

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
```

```
cctgagccag ggacgagtgc gat                                              23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gagccaggga cgagtgcgac tgt                                              23

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ctgagccagg gacgagtgcg a                                                21

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cctgagccag ggacgagt                                                    18

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ctgggactgt gcggttggga                                                  20

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ctgggactgt gcggttggga c                                                21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
```

```
ggtagagttt gacaggcaag c                                              21
```

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
ggtagagttt gacaggcaag ca                                             22
```

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
gtagagtttg acaggcaagc a                                              21
```

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

```
gtagagtttg acaggcaagc                                                20
```

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45

```
ggtagagttt gacaggcaag caa                                            23
```

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

```
cttgcctgtc taactcgcta gt                                             22
```

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

```
cttgcctgtc taactcgcta g                                              21
```

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttgcctgtct aactcgctag t                                              21

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cttgcctgtc taactcgcta                                                20

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
cttgcctgtc taactcgct                                                 19

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cttgcctgtc taactcgcta gta                                            23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cttgcctgtc taactcgcta gtt                                            23

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cttagcctgt ctaactcgct agt                                            23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gtcagagatc caaaccctcc ggt                                              23

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gtcagagatc caaaccctcc ggtt                                             24

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tcagagatcc aaaccctccg gt                                               22

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
cctgagccag ggacgagtgc ga                                               22

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gagccaggga cgagtgcgac tgt                                              23

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
cctgagccag ggacgagtgc gact                                             24

```
<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
cctgggccag ggacgagtgc ga                                              22

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tgagccaggg acgagtgcga ctgt                                            24

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cgagccaggg acgagtgcga ctgt                                            24

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gagccaggga cgagtgcgac tgc                                             23

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cctgagccag ggacgagtgc gac                                             23

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tgagccaggg acgagtgcga ctg                                             23

<210> SEQ ID NO 66
```

-continued

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tgagccaggg acgagtgcga ct                                              22

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cctgagccag ggacgagtgc gaca                                            24

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ctgagccagg gacgagtgcg act                                             23

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gagccaggga cgagtgcgac tg                                              22

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tgagccaggg acgagtgcga                                                 20

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cggggacgag tgcgactgt                                                  19

<210> SEQ ID NO 72
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ctgggactgt gcggttggga                                                   20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
cagggactgt gcggttggga                                                   20

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ctgggactgt gcggttgga                                                    19

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cacttcccgt ccttccatcc c                                                 21

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
cacttcccgt ccttccatcc ca                                                22

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
cacttcccgt ccttccatcc                                                   20

<210> SEQ ID NO 78
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 78
cacttcccgt ccttccatcc cc                                              22

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cacttcccgt ccttccatcc ct                                              22

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ccagtgcagg gtccgaggta                                                 20

<210> SEQ ID NO 81
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
uggcggcccg gcccggggcc                                                 20

<210> SEQ ID NO 82
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gtcgtatcca gtgcagggtc cgaggtattc gcactggata cgacggcccc                50

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ttataaatgg cggcccggcc                                                 20

<210> SEQ ID NO 84
<211> LENGTH: 16
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 84
cactggatac gacggc                                                         16

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
uggaaggacg ggaaguggaa g                                                   21

<210> SEQ ID NO 86
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gtcgtatcca gtgcagggtc cgaggtattc gcactggata cgaccttcca                    50

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cacgcatgga aggacggga                                                      19

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tggatacgac cttccact                                                       18

<210> SEQ ID NO 89
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ccugagccag ggacgagugc gacu                                                24

<210> SEQ ID NO 90
<211> LENGTH: 50
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 90
gtcgtatcca gtgcagggtc cgaggtattc gcactggata cgacagtcgc            50

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tcataacctg agccagggac ga                                          22

<210> SEQ ID NO 92
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tacgacagtc gcact                                                  15

<210> SEQ ID NO 93
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
cugggacugu gcgguuggga                                             20

<210> SEQ ID NO 94
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gtcgtatcca gtgcagggtc cgaggtattc gcactggata cgactcccaa            50

<210> SEQ ID NO 95
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gcttggctgg gactgtgc                                               18

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 96
tacgactccc aaccgcac                                                 18

<210> SEQ ID NO 97
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
cuugccuguc uaacucgcua gu                                            22

<210> SEQ ID NO 98
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gtcgtatcca gtgcagggtc cgaggtattc gcactggata cgacactagc              50

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gcctggcttg cctgtctaac                                               20

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ctggatacga cactagcg                                                 18

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
gguagaguuu gacaggcaag c                                             21

<210> SEQ ID NO 102
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gtcgtatcca gtgcagggtc cgaggtattc gcactggata cgacgcttgc        50

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gcccggggta gagtttgaca g        21

<210> SEQ ID NO 104
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
ctggatacga cgcttgc        17

<210> SEQ ID NO 105
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
gucagagauc caaacccucc ggu        23

<210> SEQ ID NO 106
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gtcgtatcca gtgcagggtc cgaggtattc gcactggata cgacaccgga        50

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gcctgggtca gagatccaaa cc        22

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
ctggatacga caccggag					18

<210> SEQ ID NO 109
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109 cacucccgu ccuuccaucc cc					22

<210> SEQ ID NO 110
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gtcgtatcca gtgcagggtc cgaggtattc gcactggata cgacggggat					50

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tcataacact tcccgtcctt cc					22

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ggatacgacg gggatgga					18

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tcgcacgcgc ccggcacaga c					21

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tcgcacgcgc ccggcacaga ct                                              22

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
cgcacgcgcc cggcacagac t                                               21

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gcacgcgccc ggcacagact                                                 20

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cctgagccag ggacgagt                                                   18

<210> SEQ ID NO 118
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
cctgagccag ggacgagtg                                                  19

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
cctgagccag ggacgagtgc                                                 20

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
cctgagccag ggacgagtgc ga                                              22

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cctgagccag ggacgagtgc gact                                            24

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ctgagccagg gacgagtg                                                   18

<210> SEQ ID NO 123
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ctgagccagg gacgagtgc                                                  19

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ctgagccagg gacgagtgcg a                                               21

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ctgagccagg gacgagtgcg ac                                              22

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ctgagccagg gacgagtgcg act                                             23

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 127
tgagccaggg acgagtgc                                                  18

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 128
tgagccaggg acgagtgcga                                                20

<210> SEQ ID NO 129
<211> LENGTH: 22
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 129
tgagccaggg acgagtgcga ct                                             22

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 130
tgagccaggg acgagtgcga ctg                                            23

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 131
gagccaggga cgagtgcgac                                                20

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 132
gagccaggga cgagtgcgac t                                              21

<210> SEQ ID NO 133
<211> LENGTH: 22
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 133
gagccaggga cgagtgcgac tg                                            22

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 134
agccagggac gagtgcgact                                               20

<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 135
cagggacgag tgcgactg                                                 18

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 136
ctcctgaccg cgggttccga                                               20

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 137
ctcctgaccg cgggttccga g                                             21

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 138
ctcctgaccg cgggttccga gt                                            22

```
<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
tcctgaccgc gggttccgag t                                              21

<210> SEQ ID NO 140
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ctgaccgcgg gttccgagt                                                 19

<210> SEQ ID NO 141
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
cctgggactg tgcggttg                                                  18

<210> SEQ ID NO 142
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
cctgggactg tgcggttgg                                                 19

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
cctgggactg tgcggttggg                                                20

<210> SEQ ID NO 144
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
cctgggactg tgcggttggg ac                                             22

<210> SEQ ID NO 145
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ctgggactgt gcggttgg                                                 18

<210> SEQ ID NO 146
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ctgggactgt gcggttggg                                                19

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ctgggactgt gcggttggga                                               20

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ctgggactgt gcggttggga c                                             21

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ctgggactgt gcggttggga cg                                            22

<210> SEQ ID NO 150
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
tgggactgtg cggttggg                                                 18

<210> SEQ ID NO 151
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
tgggactgtg cggttggga                                                  19

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
tgggactgtg cggttgggac                                                 20

<210> SEQ ID NO 153
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ggtagagttt gacaggca                                                   18

<210> SEQ ID NO 154
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ggtagagttt gacaggcaa                                                  19

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
ggtagagttt gacaggcaag                                                 20

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ggtagagttt gacaggcaag c                                               21

<210> SEQ ID NO 157
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 157
ggtagagttt gacaggcaag ca                                            22

<210> SEQ ID NO 158
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ggtagagttt gacaggcaag cat                                           23

<210> SEQ ID NO 159
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gtagagtttg acaggcaag                                                19

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
gtagagtttg acaggcaagc                                               20

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
gtagagtttg acaggcaagc a                                             21

<210> SEQ ID NO 162
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
agtttgacag gcaagcatg                                                19

<210> SEQ ID NO 163
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 163
agtttgacag gcaagcatgt gc                                                    22

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
agtttgacag gcaagcatgt gcg                                                   23

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
gtttgacagg caagcatgtg c                                                     21

<210> SEQ ID NO 166
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
tgacaggcaa gcatgtgcg                                                        19

<210> SEQ ID NO 167
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tagtgcttgc ctgtctaact cg                                                    22

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
agtgcttgcc tgtctaactc g                                                     21

<210> SEQ ID NO 169
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 169
tgcttgcctg tctaactcg                                                    19

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
tgcttgcctg tctaactcgc                                                   20

<210> SEQ ID NO 171
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
cttgcctgtc taactcgc                                                     18

<210> SEQ ID NO 172
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
cttgcctgtc taactcgct                                                    19

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
cttgcctgtc taactcgcta                                                   20

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
cttgcctgtc taactcgcta g                                                 21

<210> SEQ ID NO 175
<211> LENGTH: 22
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 175
cttgcctgtc taactcgcta gt                                             22

<210> SEQ ID NO 176
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ttgcctgtct aactcgcta                                                 19

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
ttgcctgtct aactcgctag                                                20

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ttgcctgtct aactcgctag t                                              21

<210> SEQ ID NO 179
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gcctgtctaa ctcgctagt                                                 19

<210> SEQ ID NO 180
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
cctgtctaac tcgctagt                                                  18

<210> SEQ ID NO 181
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 181
cagagatcca aaccctccg                                                19

<210> SEQ ID NO 182
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
ccacttcccg tccttcca                                                 18

<210> SEQ ID NO 183
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ccacttcccg tccttccat                                                19

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ccacttcccg tccttccatc                                               20

<210> SEQ ID NO 185
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ccacttcccg tccttccatc cc                                            22

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
cacttcccgt ccttccatcc                                               20

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 187
cacttcccgt ccttccatcc c                                              21

<210> SEQ ID NO 188
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
cacttcccgt ccttccatcc cc                                             22

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
acttcccgtc cttccatccc                                                20

<210> SEQ ID NO 190
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190 agaaagggt ctgcaaccaa agg                                             23

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191 gaaagggtc tgcaaccaaa                                                 20

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192 gaaagggtc tgcaaccaaa g                                               21

<210> SEQ ID NO 193
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
```

```
gaaagggtc tgcaaccaaa gg                                              22
```

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194

```
aaagggtct gcaaccaaag                                                 20
```

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195

```
aaagggtct gcaaccaaag g                                               21
```

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196

```
aaggggtctg caaccaaagg                                                20
```

<210> SEQ ID NO 197
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197

```
ctttggatcc cgacccctct tc                                             22
```

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198

```
tttggatccc gacccctctt                                                20
```

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
tttggatccc gacccctctt c                                            21

<210> SEQ ID NO 200
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
tttggatccc gacccctctt ct                                           22

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
tatatagggt cagggggttc                                              20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
gcccccggtc cctgtatata                                              20

<210> SEQ ID NO 203
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ctgagccagg gacgagtgc                                               19

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
ctgagccagg gccgagtgcg a                                            21

<210> SEQ ID NO 205
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
ctgagccagg gccgagtgcg act                                          23

```
<210> SEQ ID NO 206
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
tgagccaggg ccgagtgcga ct                                                  22

<210> SEQ ID NO 207
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
agccagggcc gagtgcgact gg                                                  22

<210> SEQ ID NO 208
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
ctgggactgt gcggttgg                                                       18

<210> SEQ ID NO 209
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ctgggactgt gcggttggg                                                      19

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ctgggactgt gcggttggga                                                     20

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ctgggactgt gcggttggga c                                                   21
```

```
<210> SEQ ID NO 212
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
tgggactgtg cggttggga                                                19

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
ggtagagttt gacaggcaag                                               20

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
ggtagagttt gacaggcaag c                                             21

<210> SEQ ID NO 215
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
ggtagagttt gacaggcaag ca                                            22

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
ggtagagttt gacaggcaag catg                                          24

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
gtagagtttg acaggcaagc                                               20
```

```
<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
gtagagtttg acaggcaagc a                                               21

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
cacttcccgt ccttccatcc c                                               21

<210> SEQ ID NO 220
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
agaaaggggt ctgcaaccaa ag                                              22

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221 aaagggtct gcaaccaaag g                                                21

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
tttggatccc gacccctctt c                                               21

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
gatggaagga cgggaagtgg aagt                                            24

<210> SEQ ID NO 224
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
gatggaagga cgggaagtgg aa                                              22

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
gatggaagga cgggaagtgg a                                               21

<210> SEQ ID NO 226
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
tctgagcctg ggtcatgcgc gacc                                            24

<210> SEQ ID NO 227
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
tctgagcctg ggtcatgcgc gac                                             23

<210> SEQ ID NO 228
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
tctgagcctg ggtcatgcgc ga                                              22

<210> SEQ ID NO 229
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
catttgggat tctgcggttg gga                                             23

<210> SEQ ID NO 230
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
tttgggagtc tgcggttggg ag                                            22

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
tttgggagtc tgcggttggg a                                             21

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
tttgggagtc tgcggttggg                                               20

<210> SEQ ID NO 233
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
tttgggagtc tgcggttgg                                                19

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ttgggagtct gcggttggga g                                             21

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ttgggagtct gcggttggga                                               20

<210> SEQ ID NO 236
<211> LENGTH: 24
<212> TYPE: DNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 236
gagagttcac tcggcacgca tgca                                            24

<210> SEQ ID NO 237
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
gagagttcac tcggcacgca tg                                              22

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
gagagttcac tcggcacgca t                                               21

<210> SEQ ID NO 239
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
agagttcact cggcacgcat gc                                              22

<210> SEQ ID NO 240
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
agagttcact cggcacgcat g                                               21

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
cgtgcttgcc tagcgaactc a                                               21

<210> SEQ ID NO 242
<211> LENGTH: 22
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 242
gtgcttgcct agcgaactca cc                                              22

<210> SEQ ID NO 243
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
tgcttgccta gcgaactcac ccg                                             23

<210> SEQ ID NO 244
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
tgcttgccta gcgaactcac cc                                              22

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
tgcttgccta gcgaactcac c                                               21

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
tgcttgccta gcgaactcac                                                 20

<210> SEQ ID NO 247
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
cttgcctagc gaactcaccc gt                                              22

<210> SEQ ID NO 248
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 248
gggggggctc gggccacctg acc                                          23

<210> SEQ ID NO 249
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
aatggaaggc gagggatgc agga                                          24

<210> SEQ ID NO 250
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
aatggaaggc gagggatgc agg                                           23

<210> SEQ ID NO 251
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
aatggaaggc gagggatgc ag                                            22

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
aatggaaggc gagggatgc a                                             21

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
aatggaaggc gagggatgc                                               20

<210> SEQ ID NO 254
<211> LENGTH: 19
<212> TYPE: DNA
<213> ORGANISM: Artificial Sequence
<220> FEATURE:
<223> OTHER INFORMATION: Description of Artificial Sequence: Synthetic
```

```
                       oligonucleotide

<400> SEQUENCE: 254
aatggaaggc gagggqatg                                                 19

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
atggaaggcg aggggatgca gg                                             22

<210> SEQ ID NO 256
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
cccatcttct gcccttccat cct                                            23

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
cacttcccgt ccttccatcc c                                              21

<210> SEQ ID NO 258
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
aatggaaggc gagggqatgc ag                                             22

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
gatggaagga cgggaagtgg a                                              21

<210> SEQ ID NO 260
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 260
aatggaaggc gagggatgc ag                                       22

<210> SEQ ID NO 261
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
cctgagccag ggacgagtgc gact                                    24

<210> SEQ ID NO 262
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
tctgagcctg ggtcatgcgc ga                                      22

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ctgggactgt gcggttggga c                                       21

<210> SEQ ID NO 264
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
tttgggagtc tgcggttggg aga                                     23

<210> SEQ ID NO 265
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
ggtagagttt gacaggcaag ca                                      22

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 266
agagttcact cggcacgcat g                                              21

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
gggggggttc gggcatctct acc                                            23

<210> SEQ ID NO 268
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
gggggggctc gggccacctg acc                                            23
```

What is claimed is:

1. An isolated nucleic acid sequence consisting of a sequence complementary to the full length of a sequence selected from the group consisting of SEQ ID NOs: 26, 27, 29-79 and 113-256.

2. A DNA-based expression vector comprising a heterologous sequence and a nucleic acid sequence consisting of a sequence selected from the group consisting of SEQ ID NOs: 26-79 and 113-256.

3. An isolated nucleic acid sequence consisting of a sequence of 12-30 nucleotides, said nucleic acid sequence including a sequence of at least 12 contiguous nucleotides complementary to a sequence selected from the group consisting SEQ ID NOs: 26-79 and 113-256, said nucleic acid sequence not consisting of a sequence complementary to the full length of SEQ ID NO:28.

4. The nucleic acid sequence of claim 1 wherein said sequence contains at least one uracil or chemically modified nucleotide.

5. The nucleic acid sequence of claim 4 wherein said chemically modified nucleotide is at least one of a 2'-modified nucleotide or a phosphorothioate backbone modification.

6. The nucleic acid sequence of claim 5 wherein said 2'-modified nucleotide is a modification selected from the group consisting of 2'-deoxy, 2'-deoxy-2'-fluoro, 2'-O-methyl, 2'-O-methoxyethyl (2'-O- MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O—NMA).

7. The nucleic acid sequence of claim 3 wherein said sequence contains at least one uracil or chemically modified nucleotide.

8. The nucleic acid sequence of claim 7 wherein said chemically modified nucleotide is at least one of a 2'-modified nucleotide or a phosphorothioate backbone modification.

9. The nucleic acid sequence of claim 8 wherein said 2'-modified nucleotide is a modification selected from the group consisting of 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-ODMAOE), 2'-O-dimethylaminopropyl (2'-O-DMAP), 2'-O-dimethylaminoethyloxyethyl (2'-O-DMAEOE), and 2'-O—N-methylacetamido (2'-O—NMA).

10. An isolated nucleic acid sequence selected from the group consisting of SEQ ID NOs: 32, 33, 34, 35, 36, 45, 51, 52, 53, 54, 55, 56, 58, 60, 61, 62, 63, 67, 71, 76 and 79, or a nucleic acid sequence encoded by a sequence selected from the group consisting of SEQ ID NOs: 32, 33, 34, 35, 36, 45, 51, 52, 53, 54, 55, 56, 58, 60, 61, 62, 63, 67, 71, 76 and 79, or a nucleic acid sequence consisting of 12-30 nucleotides wherein said nucleic acid sequence includes a sequence of at least 12 contiguous nucleotides complementary to a sequence selected from the group consisting of SEQ ID NOs: 32, 33, 34, 35, 36, 45, 51, 52, 53, 54, 55, 56, 58, 60, 61, 62, 63, 67, 71, 76 and 79.

11. A DNA-based expression vector comprising at least one nucleic acid sequence of claim 10.

12. The vector of claim 2 wherein the heterologous sequence is a heterologous promoter.

13. An isolated nucleic acid sequence
consisting of a sequence of 12-30 nucleotides, said nucleic acid sequence including a sequence of at least 12 contiguous nucleotides complementary to a sequence selected from the group consisting SEQ ID NOs: 28-38, 57-71, 117-135 and 203-207, said nucleic acid sequence not consisting of a sequence complementary to the full length of SEQ ID NO:28, or
consisting of a sequence of 12-30 nucleotides, said nucleic acid sequence including a sequence of at least 12 contiguous nucleotides complementary to a sequence selected from the group consisting SEQ ID NOs: 28-38, 57-71, 117-135 and 203-207, wherein said sequence contains at least one chemically modified nucleotide.

14. The nucleic acid sequence of claim 13 wherein said chemically modified nucleotide is at least one of a 2'-modified nucleotide or a phosphorothioate backbone modification.

15. The nucleic acid sequence of claim 14 wherein said 2'-modified nucleotide is a modification selected from the group consisting of 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O—NMA).

16. A method of treating a latent HSV-1 or HSV-2 infection in a patient comprising administering to said patient an antisense reagent specific for one or more HSV-1 or HSV-2 miRNAs in an amount sufficient to effect said treatment, said reagent comprising a nucleic acid sequence of claim 1.

17. A method of treating a latent HSV-1 or HSV-2 infection in a patient comprising administering to said patient an antisense reagent specific for one or more HSV-1 or HSV-2 miRNAs in an amount sufficient to effect said treatment, said reagent comprising a nucleic acid sequence of claim 4.

18. A method of treating a latent HSV-1 or HSV-2 infection in a patient comprising administering to said patient an antisense reagent specific for one or more HSV-1 or HSV-2 miRNAs in an amount sufficient to effect said treatment, said reagent comprising a nucleic acid sequence of claim 3.

19. A method of treating a latent HSV-1 or HSV-2 infection in a patient comprising administering to said patient an antisense reagent specific for one or more HSV-1 or HSV-2 miRNAs in an amount sufficient to effect said treatment, said reagent comprising a nucleic acid sequence of claim 7.

20. A method of treating a latent HSV-1 or HSV-2 infection in a patient comprising administering to said patient an antisense reagent specific for one or more HSV-1 or HSV-2 miRNAs in an amount sufficient to effect said treatment, said reagent comprising a nucleic acid sequence of claim 13.

* * * * *